(12) United States Patent
Bhadra et al.

(10) Patent No.: US 9,393,411 B2
(45) Date of Patent: Jul. 19, 2016

(54) SYSTEM AND METHOD OF BLADDER AND SPHINCTER CONTROL

(71) Applicant: Case Western Reserve University, Cleveland, OH (US)

(72) Inventors: Narendra Bhadra, Chesterland, OH (US); Kenneth J. Gustafson, Shaker Heights, OH (US); Tim Bruns, Cleveland Heights, OH (US); Timothy Y. Mariano, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 84 days.

(21) Appl. No.: 13/916,956

(22) Filed: Jun. 13, 2013

(65) Prior Publication Data
US 2013/0289647 A1    Oct. 31, 2013

Related U.S. Application Data

(62) Division of application No. 12/417,529, filed on Apr. 2, 2009, now abandoned.

(60) Provisional application No. 61/041,753, filed on Apr. 2, 2008.

(51) Int. Cl.
*A61N 1/36* (2006.01)

(52) U.S. Cl.
CPC ................. *A61N 1/36007* (2013.01)

(58) Field of Classification Search
CPC ............ A61N 1/36007; A61N 1/0514; A61N 1/36053; A61N 1/36057; A61N 1/3606; A61N 1/36178; A61N 1/0556; A61B 5/202; A61B 5/205; A61B 5/227
USPC ............................................. 607/39–41, 143
See application file for complete search history.

(56) References Cited

U.S. PATENT DOCUMENTS 3,650,276 A    3/1972  Burghele et al.
3,870,051 A    3/1975  Brindley et al.
(Continued)

OTHER PUBLICATIONS

Bruns, Bhadra & Gustafson, "Intraurethral Stimulation for Reflex Bladder Activation Depends on Stimulation Pattern and Location", Neurourology and Urodynamics, 2009, 6 pages.
Bhadra, N.V., et al., "Selective Suppression of sphincter activation during sacral anterior nerve root stimulation", Neurourol Urodyn 21(1), 2002, pp. 55-64.
(Continued)

*Primary Examiner* — Michael Kahelin
*Assistant Examiner* — Minh Duc Pham
(74) *Attorney, Agent, or Firm* — Tarolli, Sundheim, Covell & Tummino LLP

(57) ABSTRACT

A method and system for bladder control are disclosed. In embodiments, a method for bladder control is provided that comprises coupling an electrode to an afferent nerve that is related to the bladder. Applying a plurality of pulse burst stimulations via the electrode causes voiding of urine from the bladder. In embodiments, the plurality of pulse burst stimulations to the afferent nerve reduces external urethral sphincter (EUS) contractions and evokes bladder contractions to expel urine from the subject. In embodiments, the plurality of pulse burst stimulations to the afferent nerve evokes bladder contractions alone to expel urine from the subject. In embodiments, a system for bladder control is provided that comprises an electrode for applying a pulse burst stimulus to an afferent nerve or dermatome to reduce reflex contractions and a signal generator for generating the pulse burst stimulus.

13 Claims, 11 Drawing Sheets

(56) References Cited

U.S. PATENT DOCUMENTS

| | | | |
|---|---|---|---|
| 4,406,288 A | | 9/1983 | Horwinski et al. |
| 4,771,779 A | * | 9/1988 | Tanagho ............ A61N 1/36007 607/40 |
| 5,199,430 A | | 4/1993 | Fang et al. |
| 6,393,323 B1 | | 5/2002 | Sawan et al. |
| 7,142,925 B1 | | 11/2006 | Bhadra et al. |
| 2005/0143783 A1 | * | 6/2005 | Boveja ............... A61N 1/36007 607/40 |
| 2007/0027495 A1 | | 2/2007 | Gerber |
| 2009/0036945 A1 | * | 2/2009 | Chancellor ........ A61N 1/36007 607/39 |

OTHER PUBLICATIONS

Bhadra, NV., et al., "Selective activation of the sacral anterior roots for induction of bladder voiding", Neurourol Urodyn 25(2), 2005, pp. 185-193.

Brindley, G.S., "The first 500 patients with sacral anterior root stimulator implants: general description", Paraplegia 32(12), 1994, pp. 795-805.

Dekhuijzen, A.J., et al., "Analysis of neural bursting: nonrhythmic and rhythmic activity in isolated spinal cord." J Neurosci Methods 67 (2),1996, pp. 141-147.

* cited by examiner

SYSTEM AND METHOD OF BLADDER AND SPHINCTER CONTROL

CROSS-REFERENCE TO RELATED APPLICATIONS

The present application is a divisional application of U.S. patent application Ser. No. 12/417,529, filed on Apr. 2, 2009, which claims the benefit of U.S. Provisional Patent Application Ser. No. 61/041,753, filed Apr. 2, 2008, the entire disclosures of which are incorporated herein by reference.

FIELD OF THE INVENTION

The present invention relates to electrical stimulation of the nervous system, and particularly relates to a system and method for urinary bladder and sphincter control utilizing electrical stimulation.

BACKGROUND

Retention of urine, leading to complications such as urinary tract infection and urinary calculi, remains a major factor leading to morbidity in individuals with neurologic disorders or injury such as spinal cord injury. In high cord injury, with upper motor neuron damage, the lower nerve pathways to the bladder are intact. The aim of micturition control in these individuals is to enable them to contract the bladder musculature without direct or reflex activation of structures in the urethra that may impede urine flow. The procedure should leave an acceptable post-void residual volume within the bladder and should also be able to prevent overflow incontinence.

Previously, electrical stimulation has been applied to control the bladder and bowel. These previous attempts have predominantly focused on activation of the detrusor by sacral root or nerve stimulation, activating either motor or sensory nerves. The methods can suffer from the problem of contraction of the bladder to expel urine concurrently with contraction of the external urethral sphincter blocking urine flow. Extensive sacral dorsal rhizotomy is carried out to solve this problem in individuals with spinal cord injury. The rhizotomy technique also results in the loss of sensation and reflexes such as reflex erection in males. It would be advantageous if reflex contraction of the sphincter could be reduced or eliminated without the losses caused by the rhizotomy technique. Using continuous stimulation to activate sensory nerves to evoke reflex bladder contractions frequently results in smaller reflex bladder contractions and reduced efficiency of urine expulsion. It would be advantageous if reflex contractions of the bladder were more robust.

SUMMARY OF THE INVENTION

The present disclosure relates to a system and method for bladder control. In one aspect of the disclosure, the system comprises an electrode coupled to an afferent nerve of a subject that applies a pulse burst stimulation to reduce contractions of the urethral sphincter, and a signal generator for generating the pulse burst electrical signals. In another aspect of the disclosure, a second electrode is coupled to an afferent or efferent nerve of the subject and applies a second pulse burst stimulation to stimulate contractions of the bladder.

In another aspect of the disclosure the system and method comprises stimulating an afferent nerve with pulse burst stimulations via an electrode to reduce contractions of the external urethral sphincter while stimulating the bladder to induce micturition through the urethral sphincter. In another aspect of the disclosure, the method further comprises manually compressing the bladder. In another aspect, the system and method stimulates the bladder with pulse burst stimulations that are synchronized to the pulse burst stimulations that are applied to the afferent nerve.

In another aspect of the disclosure the system and method comprises coupling a first electrode to an intradural portion of a sacral dorsal root of a subject and coupling a second electrode to an intradural portion of a sacral ventral root of the subject. The system and method further comprises concurrently applying a first series of intermittent pulse trains to the first electrode and a second series of intermittent pulse trains to the second electrode, wherein the first and second series of intermittent pulse trains are synchronized to mitigate interference with one another and to reduce or eliminate external urethral sphincter (EUS) contractions and evoke bladder contractions to expel urine from the subject.

In another aspect of the disclosure, a system and method are provided for bladder control comprising coupling at least one electrode to at least one of an extradural nerve, pelvic nerves, a pudendal nerve, or a sacral foraminal nerve of a subject, and applying a series of intermittent pulse trains to the electrode to concurrently reduce or eliminate EUS contractions and evoke bladder contractions to expel urine from the subject.

In yet another aspect of the disclosure, a system and method for bladder control is provided that comprises attaching a dermal surface electrode or subcutaneous electrode to a skin region at or near sacral dermatomes of a subject, applying a series of intermittent pulse trains to the dermal surface electrode or subcutaneous electrode to subdue EUS contractions. In another aspect of the disclosure, a provider/subject initiated mechanical technique is performed to evoke bladder contractions to expel urine from the subject.

In yet a further aspect of the disclosure, a system and method for bladder control is provided that comprises applying an electrical signal to a sensory nerve of a subject that causes the reduction or elimination of EUS contractions and applying a motor stimulus or sensory stimulus to evoke bladder contractions to expel urine from the subject, the motor stimulus being at least one of a non-quasitrapezoidal electrical signal applied to a motor nerve or a provider/subject initiated mechanical technique.

In yet another aspect of the disclosure a system and method for bladder control is provided that comprises stimulation of an afferent nerve with pulse burst stimulations via an electrode that causes reflex bladder contractions to induce micturition. In embodiments, the electrode activates a sacral nerve, a pudendal nerve, a urethral nerve, or other sensory nerve.

In yet another aspect of the disclosure, a system and method for bladder control is provided that comprises applying an electrical signal to a sensory nerve that causes the reduction or elimination of EUS contractions, the sensory nerve being at least one of an intradural nerve, an extradural nerve, a pudendal nerve, pelvic nerves, a foraminal nerve and a dermatome. The method further comprises applying a motor stimulus to evoke bladder contractions to expel urine from the subject, the motor stimulus being at least one of a non-quasitrapezoidal electrical signal applied to a motor nerve and a provider/subject initiated mechanical technique, the motor nerve being at least one of an intradural nerve, an extradural nerve, a pudendal nerve, pelvic nerves, a foraminal nerve and a dermatome.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

The present disclosure relates to a system and method of stimulating the human nervous system via an electric signal to achieve a functional result, namely bladder control. The system and method employs a sensory feedback signal at various nerve regions of a body of a subject. In one aspect, an electrical signal causes the reduction or elimination of external urethral sphincter (EUS) contractions. In another aspect, an electrical signal enhances contraction of the bladder without encouraging contractions of the EUS. In yet another aspect, an electrical signal is used to enhance contraction of the bladder while reducing or eliminating reflexive EUS contractions. In one embodiment, a sensory feedback signal that is an artificially generated electrical signal is applied to a sensory nerve that is associated with EUS contractions, causing inhibition of natural or dysfunctional sensory signals that cause the EUS to contract. A variety of techniques for contracting the bladder in combination with the sensory feedback signal applied to the EUS are provided to facilitate the expelling of urine from a subject's body. The subject is a human or other type of species. In another embodiment, the sensory feedback signals are used to encourage EUS contractions to reduce or eliminate bladder contractions for treating incontinence.

Figure 1:
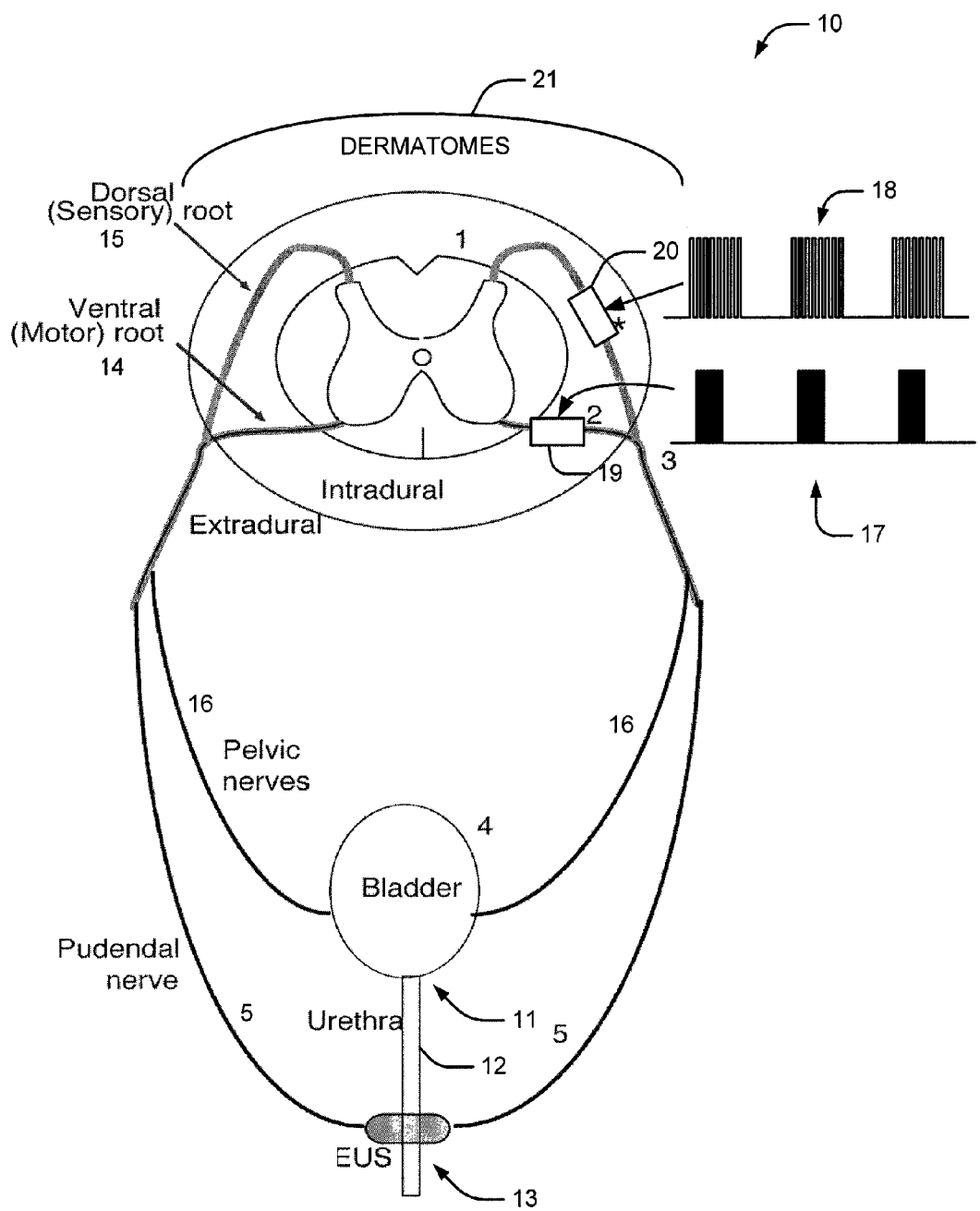
FIG. 1 is schematic illustrative embodiment of the portion of a human body wherein a first and second series of intermittent pulse trains are employed to evoke bladder contraction and to subdue EUS contractions in accordance with an aspect of the present disclosure.

Referring now to FIG. 1, there is shown an illustrative embodiment of the present disclosure within the environment of a portion of a human body 10. Urine is expelled from a bladder 4 of the body 10 of a subject through a bladder neck 11 and urethra 12 and controlled by EUS 13. Bladder 4 and EUS 13 functions are controlled by action potentials traveling to and from spinal cord 1 primarily, but not limited to, sacral roots which include ventral sacral roots 14 and dorsal sacral roots 15. Dorsal roots 15 are primarily sensory (afferent nerves) to transmit sensation to spinal cord 1, while ventral roots 14 primarily transmit motor pulses (efferent nerves) from spinal cord 1 to bladder 4 and EUS 13. Ventral roots 14 and dorsal roots 15 include both intradural nerves 2 and extradural nerves 3. The intradural nerves 2 are coupled to the spinal cord 1, while the extradural nerves 3 are intertwined and are coupled to the pelvic nerves 16 and pudendal nerve 5. The pelvic nerves 16 include ventral nerve fibers that control the contraction and relaxation of the bladder 4 and sensory nerve fibers that provide feedback to the central nervous system. The pudendal nerve 5 also includes sensory nerve fibers that provide feedback to the central nervous system to control action potentials flowing along ventral nerve fibers of the pudendal nerve 5 that cause the EUS 13 to contract, blocking the outlet from urethra 12.

When the bladder 4 is to be emptied, the flow of action potentials through the motor nerve fibers of the pudendal nerve 5 are reduced or eliminated in response to a change in the feedback of the sensory nerve fibers, which allows the EUS 13 to relax. It is to be appreciated that levator and other support muscles can also contribute to EUS 13 control. Motor nerve fibers of the pelvic nerves 16 usually carry no action potentials until the person desires to evacuate the bladder 4. At this point, action potentials are sent along the motor nerve fibers of the pelvic nerves 16 concurrently with the stopping of action potentials along the motor nerve fibers of the pudendal nerve 5, causing EUS 13 to relax and allowing bladder neck 11 to open concurrently with bladder 4 muscles contracting, thus expelling urine from the subject.

Spinal cord injuries and various other medical conditions can cause a loss of control of bladder function. To reinstitute this control, a variety of methodologies for bladder control are provided in accordance with various aspects of the disclosure. In one aspect of the disclosure, a first electrode 19 is coupled to the intradural nerves 2 of the sacral ventral root 14 and a second electrode 20 is coupled to the intradural nerves 2 of the sacral dorsal root 15. The first and second electrodes 19 and 20 are, for example, a cuff electrode, a surface mounted needle, a needle probe, or a variety of other electrode types. The electrodes 19 and 20 are, for example, coupled to respective implanted receiver stimulators that are powered and controlled by one or more signal generators 28 of FIG. 4 to provide a first series of intermittent pulse trains 17 to the first electrode 19 and a second series of intermittent pulse trains 18 to the second electrode 20. The first series of intermittent pulse trains 17 provide a motor signal to contract the bladder 4 and the second series of intermittent pulse trains 18 provide a sensory feedback signal to inhibit natural or dysfunctional signals to contract the EUS 13. The first and second series of intermittent pulse trains 17 and 18 are applied concurrently to the first and second electrodes 19 and 20 to provide electric stimulation on the sacral ventral root 14 to evoke bladder contraction and to provide electrical feedback to the sacral dorsal root 15 to subdue EUS 13 contractions.

The one or more signal generators 28 are tunable to vary one or more parameters of the motor signal and/or sensory feedback signal based on a particular subject and/or species. An exemplary signal generator 28 for performing experimental tests is the Pulsar 6pb made by FHC of Bowdoinham, Me. In embodiments, the signal generator 28 is a Pulsar 6pb combined with a DS7A made by Digitimer of Welwyn Garden City, UK. In embodiments, the signal generator 28 comprises customized or off-the-shelf parts adapted by those of ordinary skill in the art to generate the desired pulse trains 17, 18. In embodiments, the signal generator 28 is created using microcontrollers, microprocessors, or programmable logic devices with associated signal conditioning electronics. In embodiments, the signal generator 28 is an implantable pulse generator.

Figure 2A:
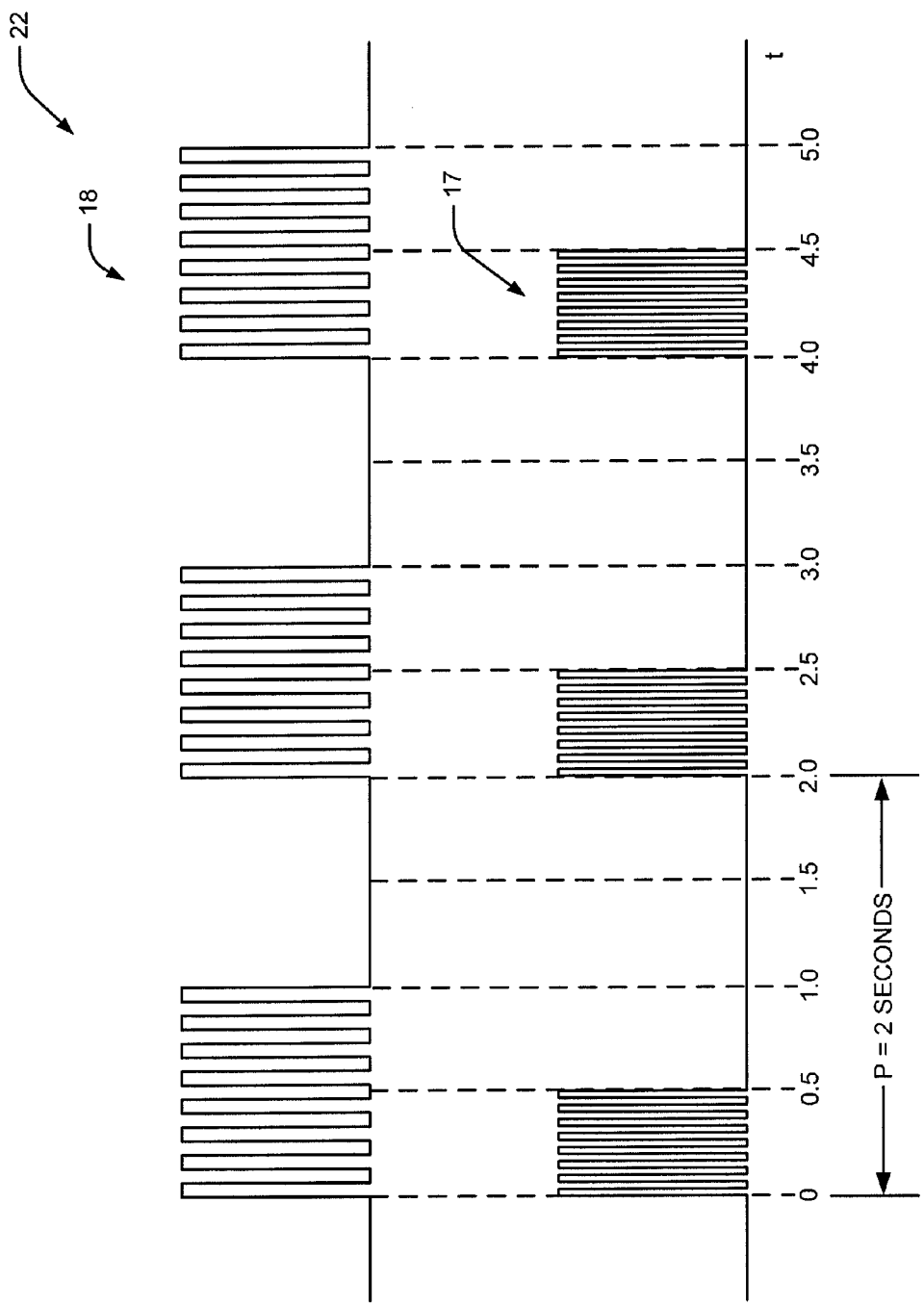
FIG. 2a illustrates an exemplary timing diagram of a first and second series of intermittent pulse trains in accordance with an aspect of the present disclosure.

In one aspect of the disclosure, the first and second series of intermittent pulse trains 17 and 18 are synchronized to mitigate coupling interference with one another during bladder evacuation. Synchronizing the first and second series of intermittent pulse trains 17 and 18, produces the least urethral 12 resistance while generating sufficient bladder drive to achieve bladder 4 emptying. FIG. 2a illustrates a timing diagram 22 of first and second series of intermittent pulse trains 17 and 18 in accordance with an aspect of the present disclosure. The first series of intermittent pulse trains 17 provides a motor signal with each pulse train 17 comprising bursts of between 2 and about 20 individual pulses 32 with pulse widths 29 of about 50 microseconds to about 300 microseconds and an inter-burst frequency 33 of about 0.25 Hz to 50 Hz. In another aspect, the individual burst comprises between 3 and about 20 discrete pulses. In yet another aspect, the individual burst comprises between 4 and about 20 discrete pulses. Each of the individual pulses within a burst has a pulse frequency 30 between about 10 Hz to about 250 Hz. The second series of intermittent pulse trains 18 provides a sensory signal with each pulse train 18 comprising bursts of 2-20 individual pulses with pulse widths 29 of about 50 microseconds to about 300 microseconds and an inter-burst frequency 33 of about 0.25 Hz to 50 Hz. Each of the individual pulses has a pulse frequency 30 of about 10 Hz to about 250 Hz. In embodiments, the pulse trains 17, 18 use identical pulse burst stimuli. In embodiments, the pulse trains 17, 18 each use differently configured pulse burst stimuli. In embodiments, the amplitudes of the first and second series of intermittent pulse trains 17 and 18 are between two and four times the nerve activation threshold.

Figure 2B:
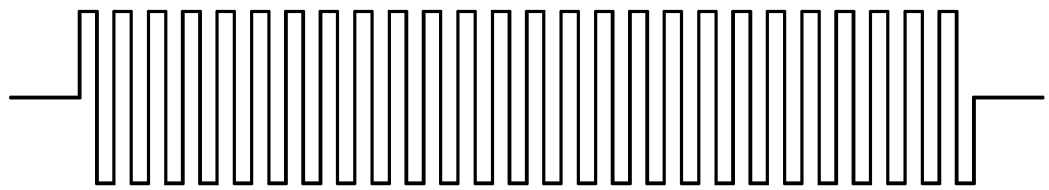
FIG. 2b illustrates an exemplary timing diagram of a continuous pulse train in accordance with an aspect of the present disclosure.
Figure 2C:
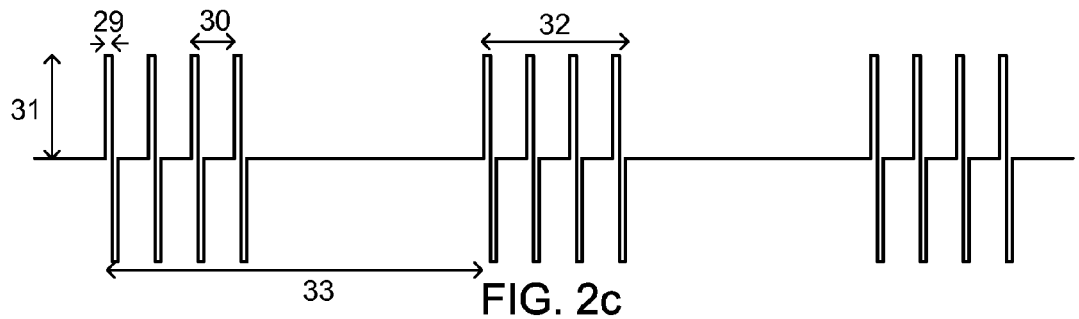
FIG. 2c illustrates an exemplary timing diagram of a pulse burst stimulus in accordance with an aspect of the present disclosure.

Referring now to FIG. 2b a continuous stimulus is presented. Unlike pulse burst stimuli, a continuous stimulus does not comprise clusters or bursts of pulses. Instead, a continuous stimulation uses a continuous series of pulses, typically at a fixed frequency to stimulate a nerve. Referring now to FIGS. 2c-2f, various embodiments of pulse burst stimuli are presented. In FIG. 2c, an embodiment of a pulse burst stimulus is illustrated with consistent pulse width 29, pulse frequency 30, also described herein as inter-pulse interval 30, pulse amplitude 31, burst width 32 or number of pulses, and inter-burst frequencies 33 (also referred to herein in the inverse as the inter-burst period). In embodiments the pulse width 29, pulse frequency 30 and inter-pulse interval 30, pulse amplitude 31, burst width 32, and/or inter-burst frequencies 33 are varied either intra-burst or inter-burst to produce a modulation of the pulse burst stimuli or a patterned pulse burst stimulus. In other embodiments the characteristics of the pulse burst stimuli (i.e. pulse amplitude 31, inter-pulse interval 30, pulse width 29, burst width 32, and inter-burst frequency 33) are selected by one of ordinary skill in the art based on the characteristics of the electrode-nervous system interaction and reflex response to achieve the desired physiological response such as suppression of the EUS reflex response or reflex excitation of the bladder 4.

Figure 2D:
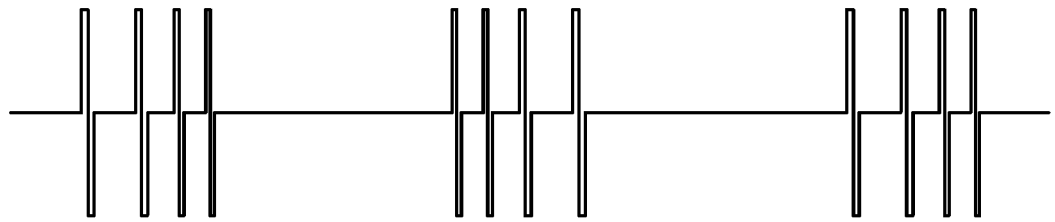
FIG. 2d illustrates an exemplary timing diagram of a frequency modulated pulse burst stimulus in accordance with an aspect of the present disclosure.
Figure 2E:
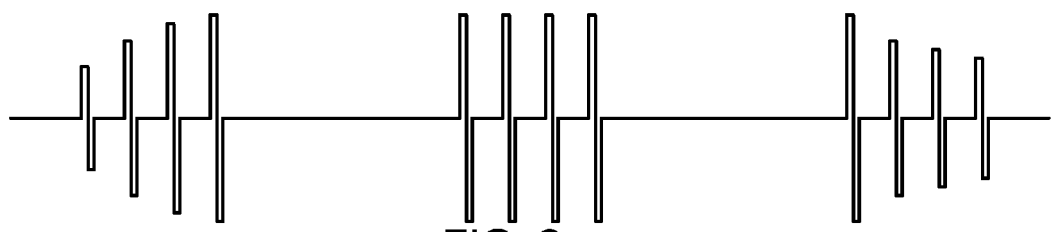
FIG. 2e illustrates an exemplary timing diagram of an amplitude modulated pulse burst stimulus in accordance with an aspect of the present disclosure.

Referring now to FIG. 2d, an embodiment of a pulse burst stimulus illustrating intra-burst frequency modulation is presented wherein the inter-pulse interval 30 between individual pulses within a single burst is varied. Referring now to FIG. 2e, another embodiment of a pulse burst stimuli illustrating both intra-burst and inter-burst amplitude 31 modulation is presented.

In other embodiments, the characteristics of the pulses that comprise the bursts are modified. In the embodiments depicted in FIG. 2a-f a bi-phasic square wave individual pulses that comprise the bursts. In other embodiments, a quasi-trapezoidal pulse is used that comprises a square leading edge followed by a plateau and an exponential trailing edge. Other pulse characteristic waveforms are readily adapted by one of ordinary skill in the art for use with a pulse burst stimuli.

Figure 2F:
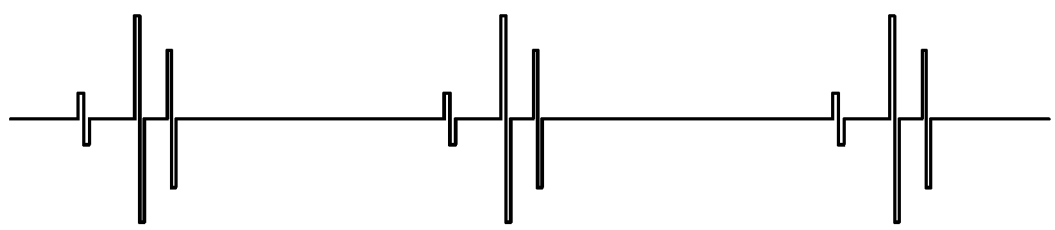
FIG. 2f illustrates an exemplary timing diagram of a pattern modulated pulse burst stimulus in accordance with an aspect of the present disclosure.

Referring now to FIG. 2f, an embodiment of a pulse burst stimulus with a pattern modulation is presented. The terms pulse burst stimulus and pulse burst stimulations are intended to cover both the consistent and varying embodiments. In embodiments, the pulse burst stimulus functions as a structured temporal code that stimulates the nervous system into responding as desired, either by contracting the bladder, as in the case of the motor signal pulse train 17 or other sensory pulse trains, or by reducing EUS contractions, as in the case of the sensory signal pulse train 18. Although the examples and descriptions herein refer principally to pulse trains 17, 18, the systems and methods are also applicable to pulse burst stimuli in general.

The motor signal 17 and sensory feedback signal 18 are synchronized in one embodiment such that the pulse trains have periods such that one period is substantially a positive integer multiple of the other. For example, the intermittent pulse trains of the sensory feedback signal are turned on and off in 1 second intervals, while the intermittent pulse trains of the motor signal are turned on for 0.5 second and off for 1.5 seconds, such that both intermittent pulse trains have a period (P) of about 2 seconds. It is to be appreciated that other numbers of pulses, frequencies, and on and off time durations are employed as long as both on and off time durations period (P) such that one period is substantially a positive integer multiple of the other. It is to be appreciated that the above motor signal and sensory inhibition signal are but examples of signals that are employed to evoke bladder contractions and reduce or eliminate EUS contractions.

Figure 3:
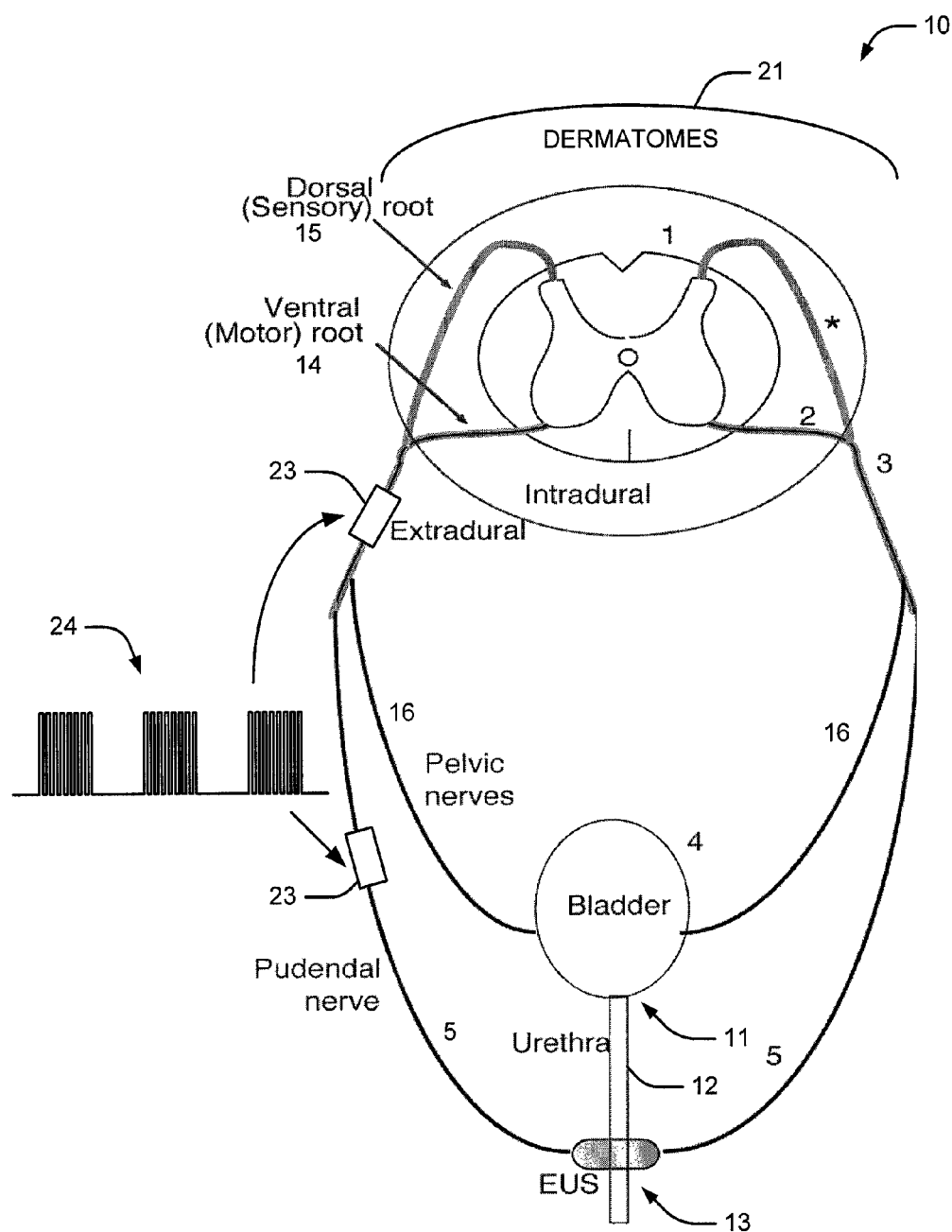
FIG. 3 is schematic illustrative embodiment of the portion of a human body wherein a single series of intermittent pulse trains are employed to concurrently evoke bladder contraction and to subdue EUS contractions in accordance with another aspect of the disclosure.

FIG. 3 is an illustrative embodiment of the portion of a human body 10 wherein a single series of intermittent pulse trains are employed to concurrently evoke bladder contraction and to subdue EUS contractions in accordance with another aspect of the disclosure. Electrode(s) 23 are coupled to extradural nerves 3 of the ventral root 14 and dorsal root 15, the pudendal nerve 5, pelvic nerves 16, sensory nerves, and/or nerves disposed in a foramen (i.e., foraminal nerves). A series of intermittent pulse trains 24 are applied to the electrode(s) 23 to evoke bladder contraction and to subdue EUS contractions. The pelvic nerves 16 include ventral nerve fibers that control the contractions of the bladder 4 that extend from the extradural nerves 3 of the ventral roots 14. The extradural nerves 3 of the ventral root 14 are intertwined with the extradural nerves 3 of the dorsal roots 15. The extradural nerves 3 of the dorsal roots 15 and ventral roots 14 extend to the pudendal nerve 5, which includes nerve fibers that control the contraction of the EUS 13.

Electrical signals applied to the extradural nerves 3, the pelvic nerves 16, the pudendal nerve 5, sensory nerves, or to foraminal nerves can cause signal coupling of the electrical signal to the other of the dorsal or ventral nerves. Therefore, a single signal in the form of the series of intermittent pulse trains 24 are employed both to evoke a motor signal for contracting the bladder 4 and as a sensory feedback signal to subdue EUS contractions. The effect on the state of the bladder 4 are modified by tuning one or more parameters associated with the series of pulse trains. It is also to be appreciated that a separate bladder drive signal and separate sensory feedback signal are applied to the extradural nerves 3, the pudendal nerve 5, the pelvic nerves 16, and/or nerves disposed in a sacral foramen.

Figure 4:
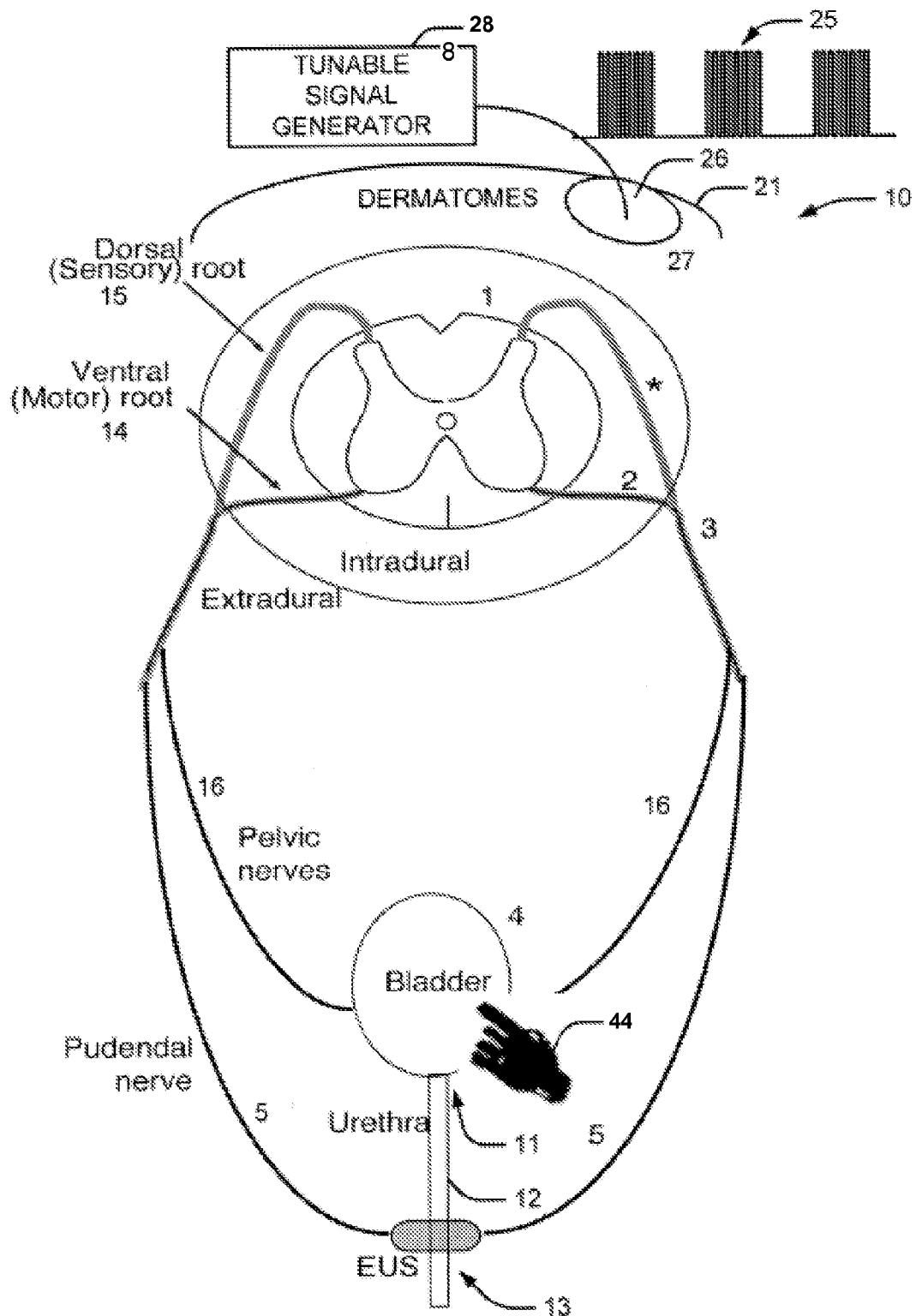
FIG. 4 is schematic illustrative embodiment of the portion of a human body wherein a series of intermittent pulse trains are applied to dermatomes to subdue EUS contractions in accordance with another aspect of the disclosure.

FIG. 4 is an illustrative embodiment of the portion of a human body 10 wherein a series of intermittent pulse trains are applied to dermatomes 21 to subdue EUS contractions in accordance with another aspect of the disclosure. One or more dermal electrodes 26 are coupled to an exterior skin region 27 at a location where a signal is coupled to the dermatomes 21 underlying the exterior skin region 27 of a subject. Alternatively or additionally, one or more subcutaneous electrodes are placed under the skin, or dermis, to be in contact with a subcutaneous surface. A series of intermittent pulse trains 25 are applied to the dermal electrode(s) 26 to subdue EUS contractions employing, for example, a tunable signal generator 28.

A variety of motor or reflex techniques are employed to contract the bladder 4. For example, a variety of different continuous or intermittent electrical signals are applied at the intradural nerves 2 and/or extradural nerves 3 of the sacral ventral root 14, at the pelvic nerve 16, at the pudendal nerve 5 or the bladder 4 wall to evoke either direct bladder contraction or indirect reflex bladder contraction. Alternatively, a variety of provider/subject initiated mechanical techniques are employed to contract the bladder 4, for example, by distension, pressing or tapping on the skin of the human body 10 at the location of the bladder 4.

FIG. 4 illustrates the pressing or tapping of the bladder 4 employing a human hand 44. In this manner, a provider/subject can initiate bladder contractions with a non-invasive technique that requires no surgical procedures. A person can simply place the dermal electrode 26 onto their skin 27 which applies the sensory feedback signal to the EUS 13 and evoke bladder contraction simply by tapping or pressing of the outside of the bladder 4 with the hand 29, thus evacuating the bladder 4 of urine.

In view of the foregoing structural and functional features described above, a methodology in accordance with various aspects of the present disclosure will be better appreciated with reference to FIGS. 5-8. While, for purposes of simplicity of explanation, the methodologies of FIG. 5-8 are shown and described as executing serially, it is to be understood and appreciated that the present disclosure is not limited by the illustrated order, as some aspects could, in accordance with the present disclosure, occur in different orders and/or concurrently with other aspects from that shown and described herein. Moreover, not all illustrated features may be required to implement a methodology in accordance with an aspect of the present disclosure.

Figure 5:
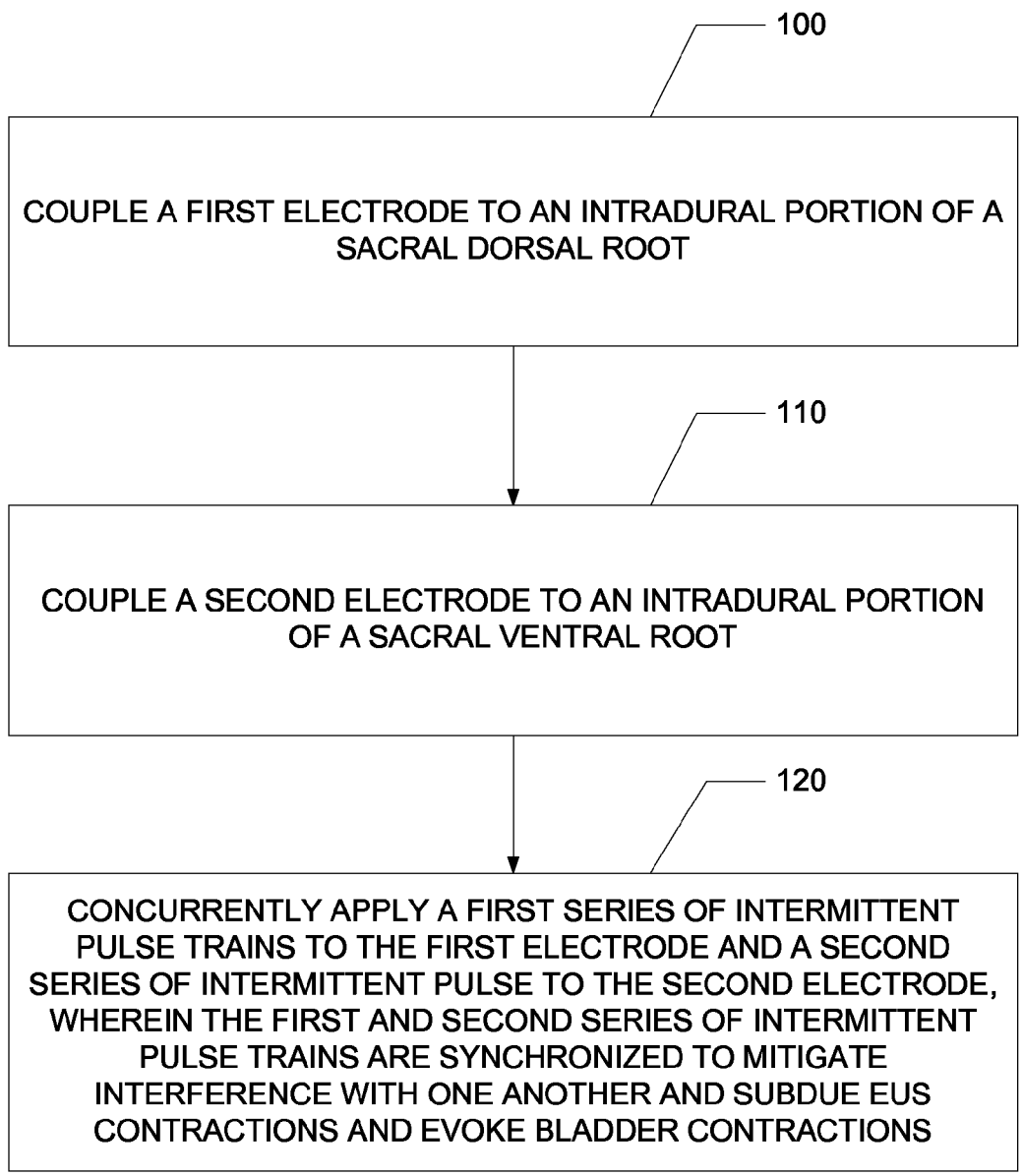
FIG. 5 illustrates a methodology for bladder control in accordance with an aspect of the present disclosure.

FIG. 5 illustrates a methodology for bladder control in accordance with an aspect of the present disclosure. At 100, a first electrode is coupled to an intradural portion of a sacral dorsal root of a subject. At 110, a second electrode is coupled to an intradural portion of a sacral ventral root of the subject. At 120, a first and second series of intermittent pulse trains are concurrently applied to the first electrode and the second electrode, wherein the first and second series of intermittent pulse trains are synchronized to mitigate interference with one another and to reduce or eliminate EUS contractions and evoke bladder contractions to expel urine from the subject.

Figure 6:
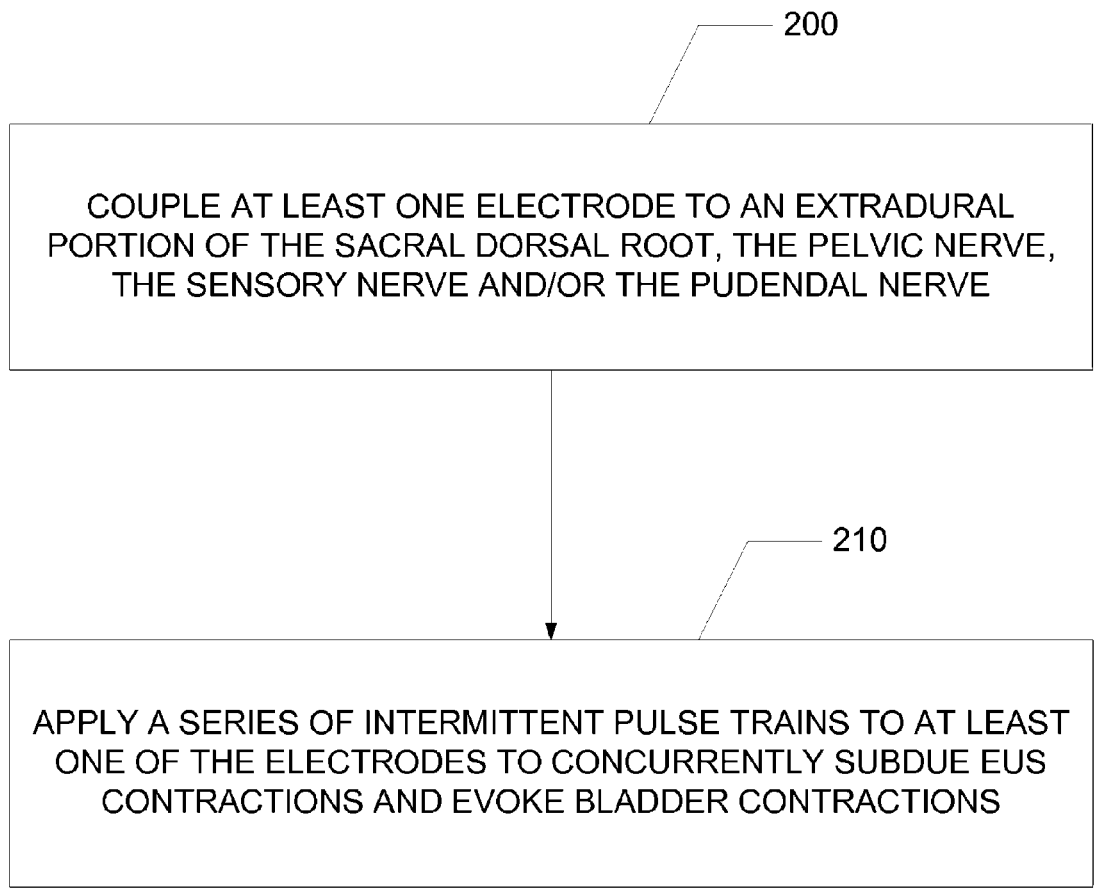
FIG. 6 illustrates another methodology for bladder control in accordance with an aspect of the present disclosure.

FIG. 6 illustrates another methodology for bladder control in accordance with an aspect of the present disclosure. At 200, at least one electrode is coupled to at least one of extradural nerves, the pudendal nerve, pelvic nerves, sensory nerves, and foraminal nerves of a subject. At 210, a series of intermittent pulse trains are applied to at least one of the electrodes to concurrently reduce or eliminate EUS contractions and evoke bladder contractions to expel urine from the subject.

Figure 7:
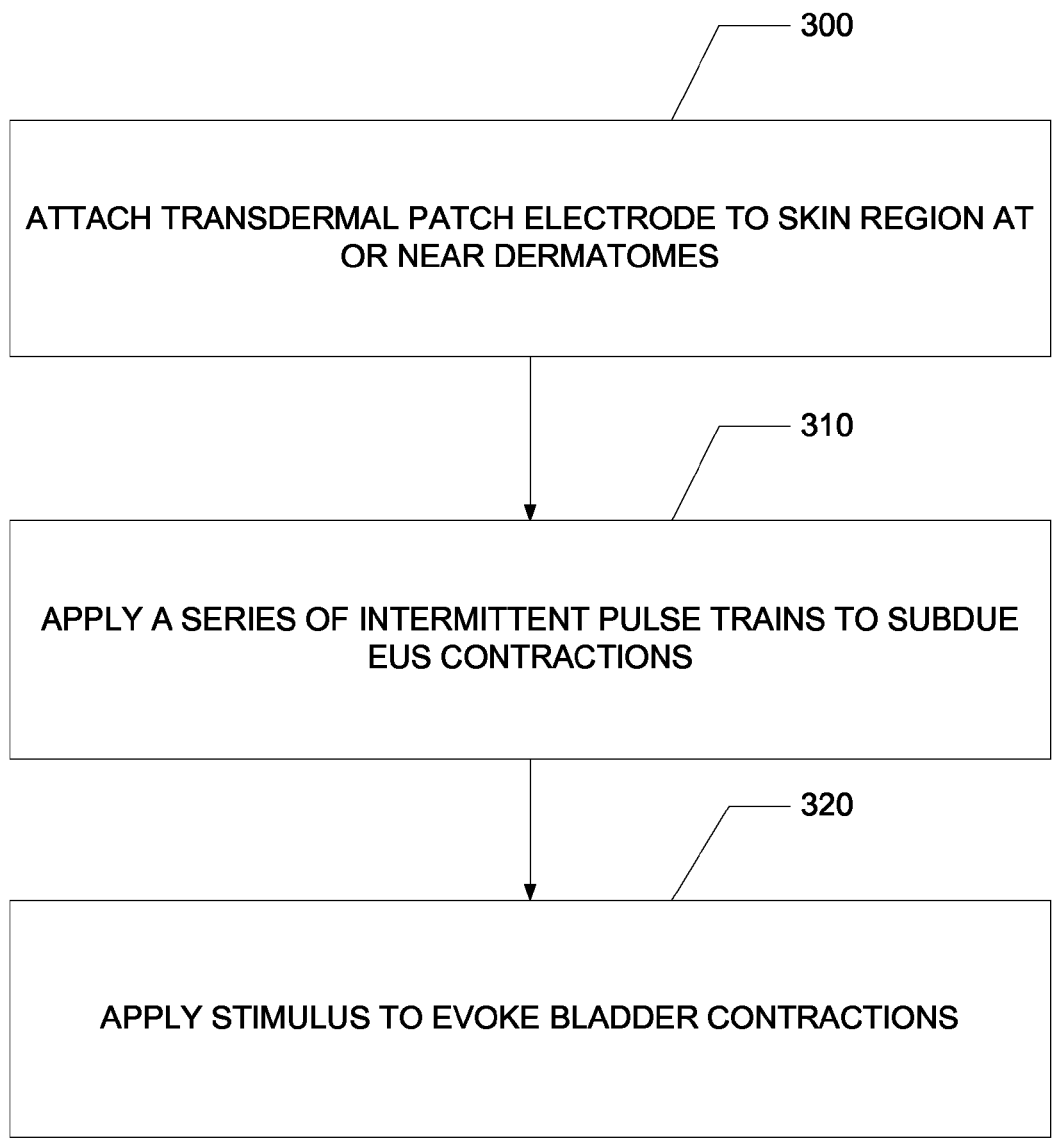
FIG. 7 illustrates another methodology for bladder control in accordance with an aspect of the present disclosure.

FIG. 7 illustrates yet another methodology for bladder control in accordance with an aspect of the present disclosure. At 300, a dermal surface electrode or subcutaneous electrode is disposed at a skin region at or near dermatomes of a subject. At 310, a series of intermittent pulse trains are applied to the electrode to reduce or eliminate EUS contractions. At 320, a motor or sensory stimulus is applied to a nerve anatomically related to the bladder 4 to evoke bladder contractions to expel urine from the subject. The bladder stimulus is provided via a non-quasitrapezoidal electric signal or a mechanical stimulus. The mechanical stimulus can be a variety of provider/subject initiated mechanical techniques such as distension, pressing or tapping on an outside area over the bladder 4 or a combination thereof.

Figure 8:
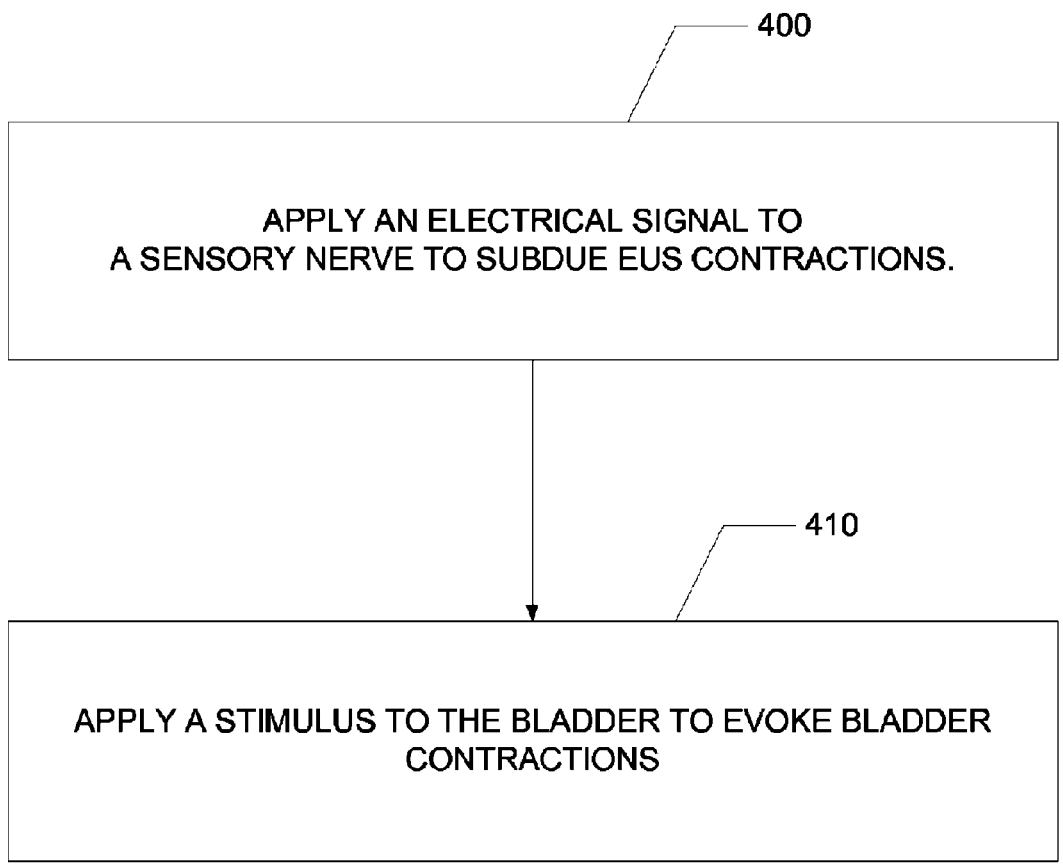
FIG. 8 illustrates another methodology for bladder control in accordance with an aspect of the present disclosure.

FIG. 8 illustrates yet a further methodology for bladder control in accordance with an aspect of the present disclosure. At 400, an electrical signal is applied to a sensory nerve of a subject to cause the reduction or elimination of EUS contractions. The sensory nerve is at least one of an intradural nerve, an extradural nerve, a pudendal nerve, a pelvic nerve, a foraminal nerve and a dermatome. At 410, a stimulus is applied to the bladder 4 to evoke bladder contractions to expel urine from the subject. The bladder stimulus is provided via non-quasitrapezoidal electric signals to a motor or sensory nerve, or a provider/subject initiated mechanical technique. The motor or sensory nerve is at least one of an intradural nerve, an extradural nerve, a pudendal nerve, a sensory nerve, a pelvic nerve, a foraminal nerve, and a dermatome. The provider/subject initiated mechanical technique is, for example, distension, pressing or tapping on an outside area over the bladder 4 or a combination thereof.

In embodiments, a pulse burst stimulus activates a nerve related to the bladder 4 to inhibit the bladder 4 from voiding to prevent incontinence. In embodiments, a pulse burst stimulus activates central pathways, for example the brain and spinal cord. In embodiments, a pulse burst stimulus activates other afferent or sensory nerves, or viscera. In embodiments, a pulse burst stimulus activates pathways for direct or reflex activation of a visceral function such as the gastro-intestinal tract, urinary tract, sexual function and hepatic function. In embodiments, a pulse burst stimulus activates peripheral sensory nerves, for example for sensory rehabilitation in neurologically impaired persons or amputees. In embodiments, a pulse burst stimulus activates central pain suppression pathways, for example in spinal cords and periphery for treating causalgia or cluster headaches. In embodiments, a pulse burst stimulus activates central or peripheral pathways for behavioral, psychiatric, or psychological disorders such as depression, schizophrenia, tics, and posttraumatic stress disorder. In embodiments, a pulse burst stimulus activates central nerve pathways in the brain or spinal cord for deep brain stimulation, thalamic and hippocampal stimulation, and spinal cord stimulation. In embodiments, a pulse burst stimulus activates afferent pathways for feedback or feed-forward control of central reflexes such as sneezing, coughing, or central pattern generators.

EXAMPLES

Reference is now made to the following examples, which together with the above descriptions; illustrate the invention in a non-limiting fashion.

Figure 9A:
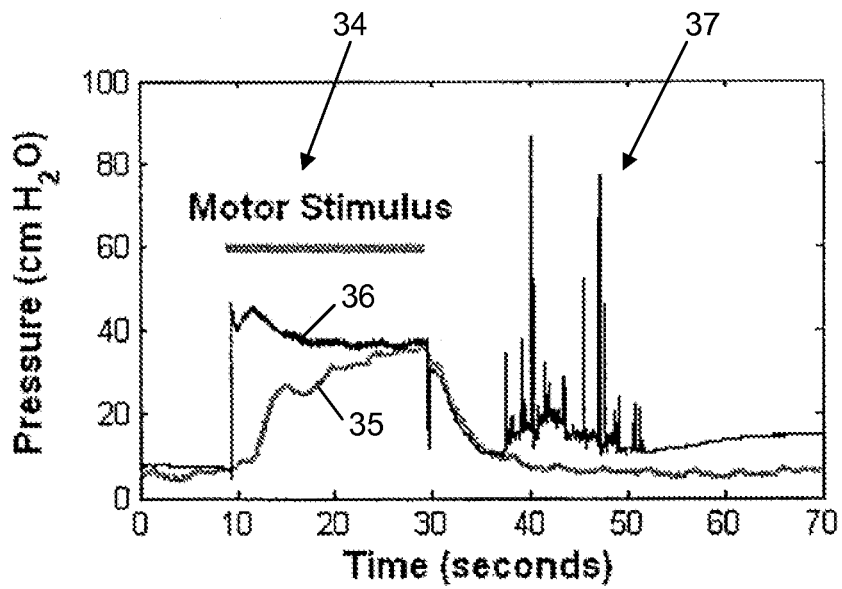
FIG. 9a illustrates undesirable EUS activity that can occur after a motor stimulus excites the bladder.
Figure 9B:
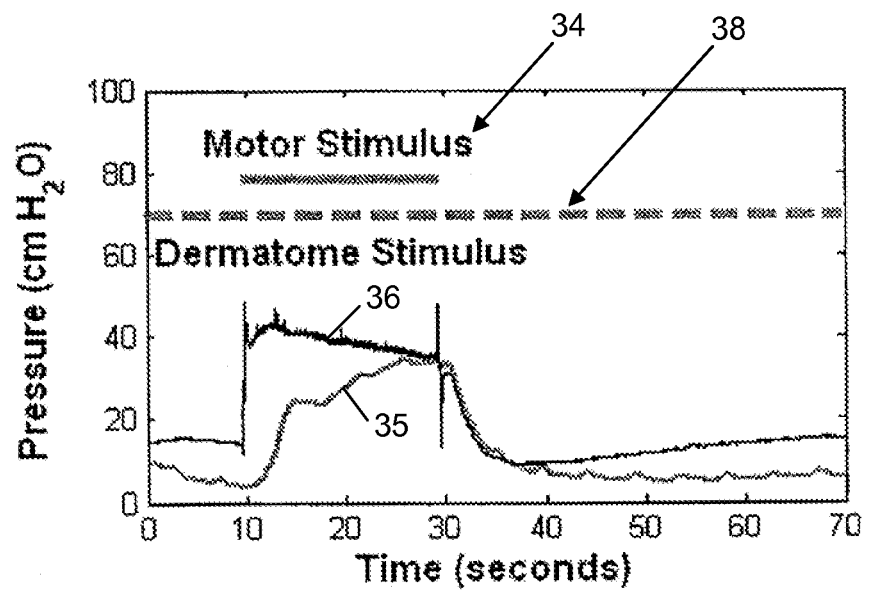
FIG. 9b illustrates elimination of undesirable EUS activity by use of a methodology in accordance with an aspect of the present disclosure.

In one exemplary set of experiments that demonstrate an embodiment of the present system and method, a motor stimulus was applied to an animal having a spinal cord injury under 15 mg/kg α-chloralose anesthesia. The motor stimulus was applied to sensory dermatomes to affect the EUS in the animal. Referring to FIG. 9a, when only a motor stimulus 34 was applied, bladder contractions 35 and EUS contractions 36 occurred during the motor stimulus 34. After the motor stimulus 34 was terminated, undesirable reflex EUS contractions 37 occurred as seen between 35 s and 55 s on the x-axis. Referring to FIG. 9b, the use of a pulse bursting stimulus 38 applied on sensory dermatomes 21 in accordance with an aspect of the disclosure eliminated the undesirable reflex EUS contractions 37 of FIG. 9a. The best dermatome bursting patterns in these experiments were a burst of 10 pulses at 20 Hz with an inter-burst frequency 33 of 1 Hz applied to the sacral dermatomes 21.

In another exemplary set of experiments that demonstrate an embodiment of the present system and method series of experiments, a stimulus was applied via a nerve cuff electrode to the pudendal nerve 5 or via an electrode placed near sensory nerves on the urethral wall in an animal under 15 mg/kg α-chloralose anesthesia. The stimulus was either a continuous pulse train between 0.5 Hz and 100 Hz or a pulse burst stimulus having the same 0.5 Hz and 100 Hz inter-burst frequency 33 but using bursts of 1-25 pulses at 33-1000 Hz instead of the continuous pulse train. Across experiments, the use of the pulse burst stimulus resulted in an average increase in evoked bladder pressure of 52.0±44.5% over the continuous pulse train stimulus. The best average bursting patterns were using a burst of 2 pulses at 200 Hz with an inter-burst frequency 33 of 20 Hz, 25 Hz, or 33 Hz, or using a burst of 5 or 10 pulses at 200 Hz with an inter-burst frequency of 1 Hz, 2 Hz, or 3 Hz depending on the animal and stimulus location.

Figure 10:
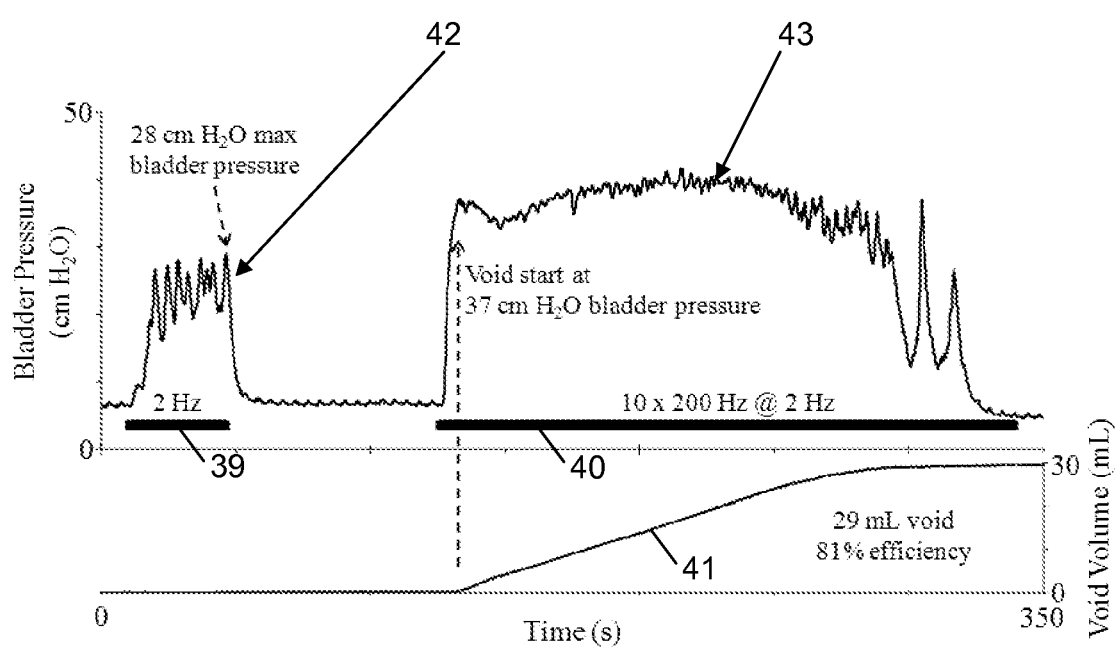
FIG. 10 illustrates a successful use of pulse bursting to evoke a larger bladder contraction and greater bladder voiding than occurs using continuous stimulation in accordance with an aspect of the present disclosure.

Referring now to FIG. 10, another exemplary experimental result of an embodiment is shown. In FIG. 10, a 2 Hz continuous pulse train 39 applied to sensory nerves originating from the urethra 12 excited 42 the bladder 4 but did not lead to any urine being expelled from the bladder 4. The subsequent use of pulse bursting 40, using 10 pulses at 200 Hz with an inter-burst frequency of 2 Hz, resulted in a larger bladder contraction 43 and successful expulsion 41 of 29 ml of urine from the bladder 4. The 81% efficiency indicated the percentage of starting volume in the bladder 4 that was emptied during the experimental trial and is a clinically desirable result.

As is appreciated by those of ordinary skill in the art, certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

Having described the invention, the following is claimed:

1. A method for bladder control, comprising:
   electrically coupling a first electrode to an afferent nerve that is anatomically related to the bladder, wherein the afferent nerve, when active, reduces external urethral sphincter contractions;
   electrically coupling a second electrode to an efferent nerve that is anatomically related to the bladder, wherein the efferent nerve, when active, evokes bladder contractions;
   stimulating the afferent nerve by applying a first series of intermittent pulse bursts by the first electrode to reduce external urethral sphincter contractions;
   concurrently stimulating the efferent nerve by applying a second series of intermittent pulse bursts by the second electrode to evoke bladder contractions;
   wherein periods of the first series of intermittent pulse bursts and the second series of intermittent pulse bursts are synchronized so that during a period, one of the first series of intermittent pulse bursts or the second series of intermittent pulse bursts has an on time that a positive integer greater than or equal to two multiple of an on time of the other of the first series of intermittent pulse bursts and the second series of intermittent pulse bursts; and
   voiding urine from the bladder via the urethra through the external urethral sphincter in response to the first series of intermittent pulse bursts and the second series of intermittent pulse bursts.

2. The method of claim 1, wherein each pulse burst of the first series of intermittent pulse bursts comprises a first pattern and each pulse burst of the second series of intermittent pulse bursts comprises a second pattern.

3. The method of claim 1, wherein the first electrode and the second electrode are selected from the group consisting of a cuff electrode, a subcutaneous electrode, a spiral electrode, a helical electrode, and a needle electrode.

4. The method of claim 1, wherein the first electrode is selected from the group consisting of a surface electrode, and a subcutaneous needle electrode.

5. The method of claim 4, wherein the first series of intermittent pulse bursts is applied to a dermatome.

6. The method of claim 1, wherein the afferent nerve is an intradural portion of a sacral dorsal root and the efferent nerve is an intradural portion of a sacral ventral root.

7. The method of claim 1, wherein the first series of intermittent pulse bursts comprises an inter-burst frequency of about 0.25 to about 50 Hz, wherein each of the pulse bursts comprises between 2 and 20 individual pulses, a width of about 10 to about 300 microseconds, and an intra-burst pulse frequency of about 10 Hz to about 250 Hz.

8. A system, comprising:
   a signal generator that generates a first series of intermittent pulse bursts and a second series of intermittent pulse bursts, wherein periods of the first series of intermittent pulse bursts and the second series of intermittent pulse bursts are synchronized so that one of the first series of intermittent pulse bursts or the second series of intermittent pulse bursts has an on time that a positive integer greater than or equal to two multiple of an on time of the other of the first series of intermittent pulse bursts and the second series of intermittent pulse bursts;

a first electrode to apply the first series of intermittent pulse bursts to an afferent nerve that is anatomically related to the bladder; and a second electrode to apply the second series of intermittent pulse bursts to an efferent nerve that is anatomically related to the bladder concurrently to the first electrode applying the first series of intermittent pulse bursts to the afferent nerve.

9. The system of claim 8, wherein the first series of intermittent pulse bursts is configured to reduce external urethral sphincter contractions; and wherein the second series of intermittent pulse bursts is configured to evoke bladder contractions.

10. The system of claim 8, wherein the first electrode is a skin electrode or a subcutaneous electrode.

11. The system of claim 10, wherein the first series of intermittent pulse bursts is applied to a dermatome via the first electrode.

12. The system of claim 8, wherein the afferent nerve is an intradural portion of a sacral dorsal root and the efferent nerve is an intradural portion of a sacral ventral root.

13. The system of claim 8, wherein the first series of intermittent pulse bursts comprises an inter-burst frequency of about 0.25 to about 50 Hz, wherein each of the pulse bursts comprises between 2 and 20 individual pulses, a width of about 10 to about 300 microseconds, and an intra-burst pulse frequency of about 10 Hz to about 250 Hz.

\* \* \* \* \*